United States Patent [19]

Dulger

[11] Patent Number: 5,762,185
[45] Date of Patent: Jun. 9, 1998

[54] ELECTRODE TRANSPORT AND STORAGE SYSTEM

[75] Inventor: Rainer Dulger, Heidelberg, Germany

[73] Assignee: ProMinent Dosiertechnik GmbH, Heidelberg, Germany

[21] Appl. No.: 455,071

[22] Filed: May 31, 1995

[30] Foreign Application Priority Data

Jun. 16, 1994 [DE] Germany .................. 44 21 062.0

[51] Int. Cl.⁶ ...................... B65D 85/20; B65D 85/30
[52] U.S. Cl. ............................. 206/207; 206/722
[58] Field of Search ................... 206/701, 722, 206/726, 205, 207; 204/420, 418, 416, 279, 419

[56] References Cited

U.S. PATENT DOCUMENTS

| 4,012,308 | 3/1977 | Jerrold-Jones et al. ............ 204/420 |
| 4,016,063 | 4/1977 | Radnoti . | |

FOREIGN PATENT DOCUMENTS

| 0 142 226 | 5/1985 | European Pat. Off. . |
| 2 429 428 | 6/1978 | France . |
| 2136023 | 1/1972 | Germany . |
| 1 773 371 | 3/1973 | Germany . |
| 3215768 | 4/1982 | Germany . |
| 8216206 U | 10/1982 | Germany . |
| 8800157 | 6/1988 | Germany . |
| 41 05 211 | 8/1992 | Germany . |
| WO 92/01218 | 1/1992 | WIPO . |

Primary Examiner—Jacob K. Ackun
Attorney, Agent, or Firm—Darby & Darby

[57] ABSTRACT

An electrode transport and storage system has an electrode with a sensor portion and an enclosure into which at least the sensor portion of the electrode projects and which together with the electrode encloses a storage chamber designed to contain a liquid for providing improved storage and transport for the electrode. The enclosure is formed as a rigid casing which is connected at the open end of the casing with the electrode. A sealing element is provided in-between the casing and the electrode. The storage chamber is filled with an electrolyte solution which immerses at least the sensor portion of the electrode while the sealing element retains the solution during transport and storage of the electrode. If desired, the electrode may be calibrated within the casing which is filled with a calibration solution.

16 Claims, 1 Drawing Sheet

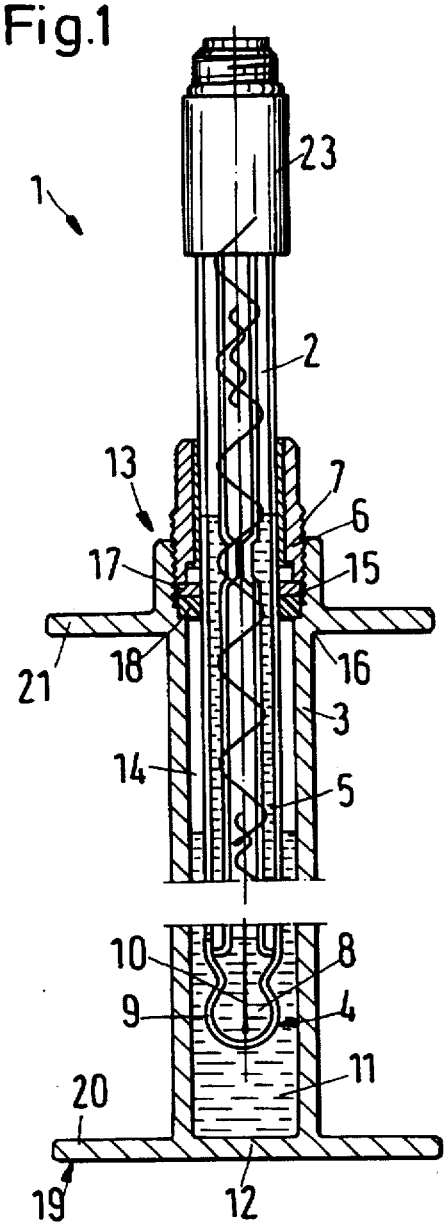
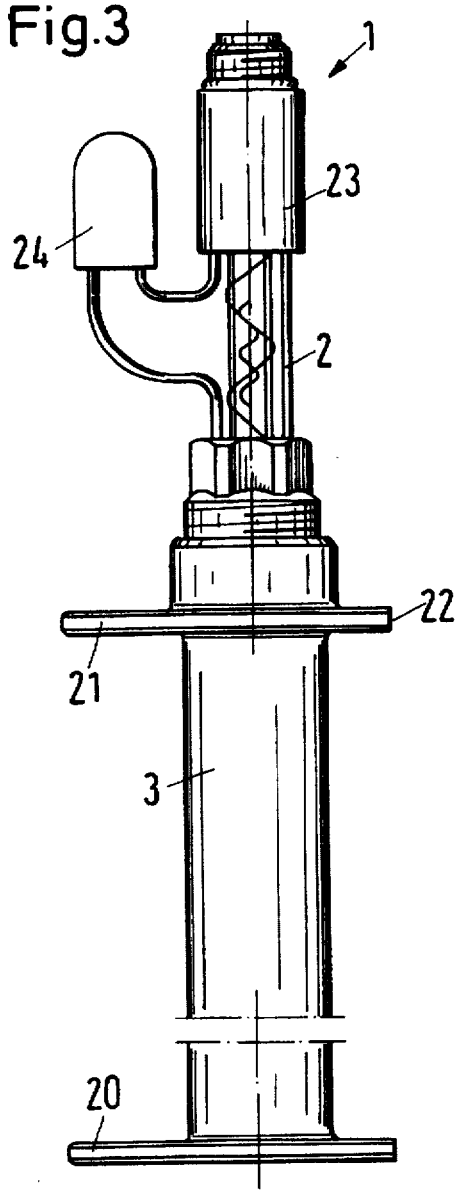
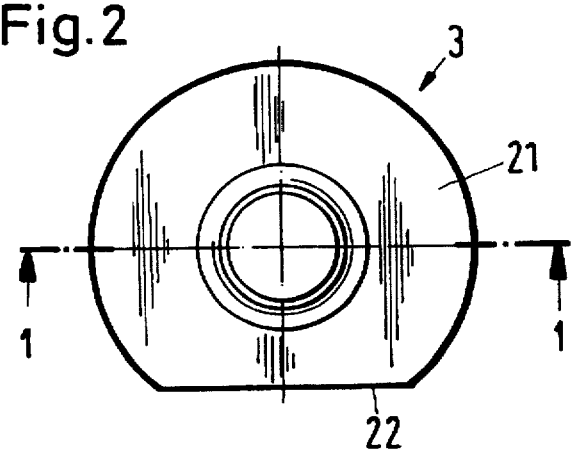

5,762,185

ELECTRODE TRANSPORT AND STORAGE SYSTEM

FIELD OF THE INVENTION

This invention relates to a system for transporting and storing electrodes, and more particularly to a system for transporting and storing an electrode and a casing, into which at least the sensitive portion of the electrode projects and which, together with the electrode, defines a storage space for a liquid, and a procedure for the exchange or replacement of electrodes using such electrode storage and transport system.

BACKGROUND OF THE INVENTION

Electrochemical measuring and test electrodes such as pH and redox electrodes must be stored in a liquid. Specifically, the sensitive portion of the electrode, where the electrochemical processes take place, must be immersed in a storage solution for the entire duration of the storage, including the time in transit from the manufacturer to the user. For this purpose, an electrolyte solution is generally used.

For transporting and storing such measuring or test electrodes, the traditional medium has been electrolyte-filled silicone caps approximately the size of a thimble, into which the sensitive portion or tip of the electrode is inserted. In conventional systems, these silicone caps serve as the storage vessel for the electrolyte solution for the entire duration of storage, until the electrode is used. The elasticity of the silicone caps allows each cap to cling relatively closely to the electrode tip, thus fairly sealing off the storage space or chamber, and preventing the leaking of the electrolyte solution from the storage chamber.

The problem, however, is that most of the solutions used for storing electrodes have a strong film-creeping tendency. Therefore, although the silicone caps cling to the electrode, the solution escapes from the storage chamber and the caps dry out. While this process may take several weeks or even months, it nevertheless limits the shelf life of the electrodes concerned. Traditionally, these electrodes cannot be stored longer than six months prior to their use. Storage limitations of this type necessitate a relatively quick turnover of the electrodes and thus complicate the storage of electrodes that are not used frequently.

SUMMARY OF THE INVENTION

Accordingly, it is an object of the present invention to provide an improved storage and transport system for test electrodes.

It is a further object of the present invention to provide a system for transporting and storing electrodes, of the type mentioned above, in which the casing is designed as a rigid enclosure, connected to the electrode and having a sealing element positioned in-between the casing and the electrode.

This design makes it possible to retain the storage solution for the electrode in the storage chamber with a higher degree of reliability. The electrode and the casing are rigid; therefore, exposure to certain pressures will not deform the casing noticeably. This design thus makes it possible to obtain a better seal between the casing and the electrode by means of a sealing element. The sealing effect is of a sufficient magnitude to prevent creeping of the storage solution with a higher degree of dependability. If indeed there is some creeping, the leakage is generally so minor that even after prolonged storage, there will be sufficient storage solution left in the casing to adequately protect at least the sensitive portion of the electrode.

The shelf life of the electrodes can thus be extended to eight or more months and storage is simplified. Longer-range logistics planning is possible, and even infrequently used types of electrodes can be stored and kept available at less cost.

The connecting element between the electrode and the casing need not be of the positive locking type. The connecting element requires minimal holding strength, which can be accomplished by a simple plug-in approach and only needs sufficient strength for reliably holding the electrode in the casing while at the same time exerting pressure on the sealing element. In this way, the sealing element fits tightly between the casing and the electrode without leaving any gaps or other openings through which the storage solution may escape from the storage chamber. The casing offers an additional benefit in that the electrode is not only immersed in a solution but is also mechanically protected, which is particularly useful when shipping and transporting the electrodes.

In a preferred embodiment, the electrode incorporates a shaft that extends from a mount to a tip, which includes the sensitive portion, with the casing extending over at least the length of the shaft. Given that the shaft is a mechanically vulnerable element, this particular design provides adequate protection of the shaft by the casing. The electrode mount is a standard feature, used at the testing location to attach the electrode to a given test instrument. If the casing extends at least over the length of the shaft, the electrode may be fastened to the casing by means of the mount which is standard on every electrode. Therefore, no further modifications to the electrode are necessary and the electrode is held in the casing as fly as in the test instrument.

The casing preferably has a space between it and the electrode such that the shaft is surrounded by a safety zone on all sides. In this way, minor impacts on the casing will not be transferred to the electrode's shaft. Furthermore, this design assures exposure of the electrode shaft, and in particular the sensitive portion, to the storage solution which surrounds the shaft on all sides. No part of the shaft touches the wall of the casing, thus ensuring that the appropriate portion of the electrode is fully exposed to the solution.

Preferably, the casing has a solution-inspection window or is formed of a transparent material, which permits visual checking of the storage solution level such as the electrolyte in the casing. If the level of the solution has actually dropped to a point where the desired storage conditions are no longer assured, the storage solution can be replenished.

Preferably, the electrode mount is provided with an outside thread and the open end of the casing with an inside thread so that the electrode and the casing can be threadably engaged. Most test electrodes come with an outside thread, allowing them to be threadably engaged into a test instrument at the test site. This same thread can serve to fasten the electrode in the casing which will mount the electrode in the casing firmly enough to hold it securely in the desired position.

Preferably, the sealing element is positioned next to the outside thread such that the seal is located directly at the threaded connection. A relatively precise fit exists between the casing and the electrode so that the sealing element can provide a high degree of dependability without any specific design effort.

The sealing element preferably incorporates an O-ring-type gasket pressed in-between an annular ledge on the electrode and an annular shoulder within the casing. The pressure on the gasket is thus axial, i.e. in the direction of the longitudinal axis of the electrode and of the casing, which is also the direction in which the electrode is inserted in the casing. It is thus possible to apply the necessary sealing pressure without having to redesign the casings of conventional electrodes.

At its closed end, the casing is preferably provided with an outwardly extending base which offers the advantage of permitting the placement of the casing containing the electrode for storage in an upright position, for example on a shelf. In this position, it is relatively easy to check the level of the solution. Since in most cases, the sensitive portion, i.e. the sensor of the electrode, is located at the tip of the shaft, the sensor portion will project farthest into the casing. As a result, the sensor is immersed more deeply into the storage solution than the rest of the shaft, which is desirable as it is primarily the sensor that must be surrounded by the solution. Thus, if the level of the solution were to decrease, the sensor portion of the electrode would be affected relatively late in the process. Therefore, even if there is a minor loss of solution, the shelf life of the electrode would not be significantly affected. By increasing only the diameter of the base, it is unnecessary to enlarge the storage chamber and the amount of storage solution needed can thus be minimized.

The base is preferably designed as an annular collar for more convenient handling, in contrast to individual protrusions or legs on conventional electrodes, which can snag and/or injure the individual handling the electrode.

The casing is preferably provided with a second annular collar, positioned adjacent the open end. The second collar is designed to protect the portion of the electrode that protrudes from the casing. If the casing is laid down sideways, the electrode portion protruding from the casing will thus always remain above the contact surface, assuming the casing is properly weighted. This is especially true when the center of gravity of the electrode system is between the second collar and the closed end of the casing.

The second collar is preferably located in the area of the connection between the casing and the electrode. The second collar thus mechanically reinforces the casing at the point where it is exposed to the strongest radial pressures. This reinforcement obviates the need for excessive precaution when inserting the electrode into the casing. Also, the sealing strength is improved when threadably engaging the casing and electrode together as a relatively strong pressure may be applied.

Preferably, the perimeter of the first and/or the second collar is provided with a non-circular feature which will prevent the electrode from rolling off a table or shelf if the electrode is turned over. Instead, the electrode will come to a stop as soon as the non-circular feature reaches the surface of the table or shelf.

The non-circular feature is preferably provided in the form of a truncation of the annular collar, which is relatively easy to manufacture. As an added advantage, the individual units can be moved closer together during storage depending upon the size and number of truncations.

It will also be advantageous to align the truncations of the first and the second collar in the axial or longitudinal direction. In this way, the system will always lie in a specific orientation if it were to fall over or be set down sideways. This feature can be used for additional inspection purposes as it can be observed, even in a vertical orientation, whether the electrode or its sensor portion is still covered by the storage solution.

The casing is preferably formed of a material resistant to calibrating solutions. This permits the use of the casing as a calibration vessel in the initial preparation of an electrode. Practically all electrodes must be calibrated prior to their first use, i.e. they must be immersed in a calibrating (buffer) solution while the test or measuring instrument is adjusted to a particular setting. If the casing can be used for calibration, no additional vessels are needed. The ability of the casing to fly stand upright is a particular advantage in this context since the calibration process typically involves extended immersion of the electrode in the buffer solution while both hands are needed for adjusting the test instrument.

The casing is preferably formed by injection molding, which is generally inexpensive to manufacture yet can be formed with the necessary precision, a desirable feature especially for the area where the electrode connects to the casing. The material used is preferably a plastic such as polycarbonate.

It is desirable to keep the storage space filled with storage solution to a level of at least 80% of capacity. However, filling the storage space completely is not generally necessary and in most cases not even desirable since an allowance should be made for thermal expansion of the electrolyte solution. Filling the storage space to an indicator level provides relative assurance that even after prolonged storage there remains at least enough solution to cover the sensor portion.

This invention also covers a method for replacing electrodes used by the electrode transport and storage system as described above, whereby a fresh, i.e. new electrode, is taken from the electrode transport and storage system, a used electrode is removed from the test instrument, the new electrode is installed in the test instrument and the used electrode is re-inserted in the casing of the electrode transport and storage system.

A major advantage of the casing when using this replacement method is reusability. Test electrodes, and in particular pH and redox electrodes, are still limited in terms of the state of the art in that they have a relatively short product life, i.e. they must be replaced at least once every 12 to 14 months. Since these test electrodes are filled with electrolyte and precious metals, they must be separated for environmental considerations and cannot always be easily discarded. Using the preferred electrode transport and storage system when exchanging the electrodes, the used electrode is repacked and shipped either back to the manufacturer or to an appropriate collection point. The shipping container is in the form of the casing which is available with the delivery of the new electrode, so that used electrodes may be returned. The repacking and return of the casing may be prepared by preaddressing the electrode transport and storage system for return shipment, with the used electrode, to a particular disposal point.

It is also desirable to calibrate the new electrode in a calibration solution within the casing, prior to installing the electrode in the test instrument. Therefore, the preferred casing serves as the calibration vessel.

BRIEF DESCRIPTION OF THE DRAWINGS

FIG. 1 is a cross-sectional view of the preferred electrode transport and storage system along line I—I of FIG. 2 according to the present invention.

FIG. 2 is a top view of the preferred casing according to the present invention.

FIG. 3 is a side view of the preferred electrode transport and storage system according to the present invention.

DETAILED DESCRIPTION OF THE INVENTION

Referring to FIG. 1, a preferred electrode transport and storage system 1 includes an electrode 2 and a casing 3. The electrode 2 is an electrochemical test electrode with a sensor portion 4 located at the tip of a shaft 5. The shaft extends from the sensor portion 4 to a threaded bushing 6, having an outer thread 7 which is conventional in the art. The outer thread 7 threadably engages the electrode 2 into a test instrument for the stationary measuring of parameters for which the instrument is intended, such as the pH value or the redox potential. The internal design of this type of electrode is also essentially conventional. The electrode 2 often contains an electrolyte 8 and a metal 10, especially a precious metal such as silver. The electrolyte 8 is covered by a membrane 9 which constitutes the outer surface of the sensor portion 4. During storage and transport of the electrode 2, this sensor portion 4 must be permanently immersed in a storage liquid 11 such as KC1.

The casing 3 is a tubular cylinder with a closed end 12 and an open end 13. The casing 3 thus forms a storage space or chamber 14 which is filled to at least 80% of its volume with the electrolyte solution 11. For clarity's sake, part of the length of the casing 3 and the electrode 2 is not shown in FIGS. 1 and 3.

At its open end 13, the casing 3 is provided with an inner thread 15 which engages the outer thread 7 of the electrode 2. The electrode is usually factory-supplied with an O-ring 16 which is located at the shaft end of the inner thread 15 and is flush with an annular ledge 17 of the threaded bushing 6. When the units are threadably engaged, the O-ring 16 is pressed against an annular shoulder 18 in the casing 3. Even when the electrode 2 is hand-threaded into the casing 3, the O-ring 16 will seal the connection between the casing 3 and the electrode 2 sufficiently to prevent virtually any loss of storage solution 11 even if the latter has a strong tendency to creep. When the electrode 2 is later used, the O-ring 16 also serves to seal the test area which allows for early detection of any damage to the O-ring 16. If the level of the solution 11 in the chamber 14 decreases during storage, it may indicate that the O-ring is not sealing properly.

At its closed end 12, the casing 3 is provided with an enlarged base 19 formed by an annular collar 20, which is flush with the closed end 12 of the casing 3. The collar 20 significantly improves the steadiness of the casing 3, allowing the electrodes 2 to be stored in an upright position. Upright storage ensures that the sensor portion 4 of the electrode 2 is immersed in the storage solution 11 to the maximum level possible. Even if the level of the storage solution in the storage chamber 14 decreases, it would take a relatively long time before the sensor portion 4 dries out.

The improved steadiness provided by the collar 20 offers an additional advantage. Prior to their first use, the electrodes 2 generally have to be calibrated, which involves immersion in a buffer solution while the test instrument is adjusted to a specific setting. While the electrode 2 is immersed in the buffer solution for an extended period of time, both hands are generally needed to adjust the test instrument. Since the casing 3 now has a much steadier base, it is capable of being used as the calibration vessel. In this way, the storage chamber 14 can be filled with the calibrating buffer solution and the electrode 2 can be reinserted into the casing 3. Since the storage chamber 14 is relatively small in volume, the amount of calibration solution needed is correspondingly small.

The casing 3 is also provided with a second annular collar 21 located next to its open end 13, as close as possible to the connection between the electrode 2 and the casing 3. As shown in FIG. 1, the second collar 21 is located at the point where the O-ring 16 is pressed in-between the threadably engaged electrode 2 and casing 3. At this point, the second collar 21 gives the casing 3 improved strength in a radial direction, permitting the use of greater sealing pressures.

Referring to FIGS. 2 and 3, the two collars 20 and 21 are truncated, i.e. they incorporate a section 22 which deviates from their otherwise annular form. In essence, the section 22 is formed as a chord on a circle. Preferably, the sections 22 of the two collars 20, 21 are aligned with each other in the longitudinal direction. If during storage or transport, the system 1 were to fall over, this configuration will prevent damage to the system 1 by preventing the system from rolling. Rather, the system 1 will come to a stop when section 22 engages a flat surface. Even if the electrode falls over, the system 1 will not roll off a table or shelf unless extreme conditions are present. In the alternate embodiment, the collars 20 and 21 could have a plurality of sections 22 without deviating with the intent of the invention.

While the first collar 20 provides improved steadiness in an upright or vertical orientation, as shown in FIGS. 1 and 3, the second collar 21 serves to protect the section 23 of the electrode 2 protruding from the casing 3, against damage when the system 1 lies sideways, i.e. when the shaft 5 is in a horizontal orientation. For that purpose, the center of gravity of the system is preferably between the collar 21 and the closed end 12. As a result, whenever the system 1 is in a horizontal orientation, the system will rest on the collars 20 and 21, but not on the section 23. This will occur even if the section 23 is equipped with laterally protruding accessories 24 (FIG. 3), as long as these accessories 24 do not extend beyond the second collar 21.

When the electrode is inserted into the casing 3, the storage chamber 14 is filled to at least 80% of its capacity to assure that the sensor portion 4 is covered by the storage solution 11 even when the system 1 is in a horizontal orientation.

Preferably, the casing 3 is made of a transparent plastic material so as to permit inspection of the fill level of the solution 11 at any time. Alternatively, the casing 3 can be provided with a viewing window, not illustrated.

The casing 3 is preferably rigid and surrounds the shaft 5 of the electrode 2 at a specific distance on all sides. When subjected to external forces such as minor impacts or shocks, the casing 3 will not significantly deform. In other words, the casing 3 will not contact the shaft 5 nor the sensor portion 4 of the electrode 2. This provides both mechanical protection for the electrode 2 and the assurance that at least the sensor portion 4 will be continuously surrounded on all sides by the electrolyte solution 11. In addition, there will not be any change in the electrode 2 resulting from contact between the sensor portion 4 and the casing 3.

A significant benefit of the electrode system 1 is that the casing 3 is reusable. Many electrochemical test electrodes, and in particular pH and redox electrodes, are technically limited to a relatively short product life, i.e. they must be replaced with a new electrode at least once every 12 to 14 months. Since most of these electrochemical test electrodes are filled with electrolyte as well as precious metals, they have to be separated. This poses a problem in terms of disposal as most users are not equipped to handle the disposal of this type of electrode.

This problem is relatively easy to alleviate by means of the casing 3 of the electrode system 1 in which the new electrode is delivered. If desired, the new electrode 2 can be calibrated in the casing 3, afterwhich the electrode 2 is mounted in the test position. The casing 3 is now available to receive the used electrode, which is removed from the test instrument. Protected by the casing 3, the used electrode can be shipped to a disposal point or returned to the manufacturer.

While the embodiment of the invention shown and described is fully capable of achieving the results desired, it is to be understood that this embodiment has been shown and described for purposes of illustration only and not for purposes of limitation. Other variations in the form and details that occur to those skilled in the art and which are within the spirit and scope of the invention are not specifically addressed. Therefore, the invention is limited only by the appended claims.

What is claimed is:

1. An electrode transport and storage system, comprising:
   an electrode having a sensor portion, said electrode having an outer thread;
   an enclosure into which at least said sensor portion of said electrode projects, wherein said enclosure has a rigid casing having an open end and closed end, said open end of said casing has an inner thread, said casing connected to said electrode at said open end by way of said inner thread of said casing open end threadably engaging said outer thread of said electrode;
   a storage chamber formed by said electrode and said enclosure at said closed end, said storage chamber for storing a liquid which at least partially immerses said electrode in said liquid; and
   a sealing element pressed between said casing and said electrode for retaining said liquid within said storage chamber during transportation and storage of said electrode.

2. The system of claim 1, wherein said electrode includes a shaft which extends from a mount to a tip, wherein said tip includes said sensor portion and said casing extends at least over the length of said shaft.

3. The system of claim 2, wherein said casing surrounds said shaft at a specific distance on all sides.

4. The system of claim 1, wherein said casing is provided with at least one of a liquid-level inspection window and a transparent material.

5. The system of claim 1, wherein said sealing element is positioned adjacent to said outer thread.

6. The system of claim 1, wherein said sealing element comprises an O-ring provided between an annular ledge on said electrode and an annular shoulder within said casing.

7. An electrode transport and storage system, comprising:
   an electrode having a sensor portion;
   an enclosure into which at least said sensor portion of said electrode projects, wherein said enclosure has a rigid casing having an open end and closed end, said casing connected to said electrode at said open end, said casing terminating in an outwardly extended base stand at said closed end;
   a storage chamber formed by said electrode and said enclosure at said closed end, said storage chamber for storing a liquid which at least partially immerses said electrode in said liquid; and
   a sealing element provided between said casing and said electrode for retaining said liquid within said storage chamber during transportation and storage of said electrode.

8. The system of claim 8, wherein said base stand consists of an annular collar.

9. The system of claim 9, wherein said casing is provided with a second annular collar adjacent said open end.

10. The system of claim 9, wherein said second collar is located in an area in which said casing connects to said electrode.

11. The system of claim 9, wherein in the circumferential direction, at least one of said first and said second collars incorporates a non-circular feature.

12. The system of claim 11, wherein said non-circular feature comprises a truncation.

13. The system of claim 11, wherein said first and second collars incorporate a non-circular feature, both of which are aligned with each other.

14. The system of claim 1, wherein said casing comprises a material which does not chemically react to calibration solutions.

15. The system of claim 1, wherein said casing is formed by injection-molding.

16. The system of claim 1, wherein at least 80% of the volume of said storage chamber is filled with said liquid.

* * * * *